United States Patent
Hennig

(10) Patent No.: US 6,524,306 B1
(45) Date of Patent: Feb. 25, 2003

(54) LOCK DEVICE FOR SURGICAL INSTRUMENTS

(75) Inventor: Rune Hennig, Tromsø (NO)

(73) Assignee: Elekta AB, Stockholm (SE)

( * ) Notice: Subject to any disclaimer, the term of this patent is extended or adjusted under 35 U.S.C. 154(b) by 0 days.

(21) Appl. No.: 09/600,586

(22) PCT Filed: Jan. 20, 1999

(86) PCT No.: PCT/NO99/00016

§ 371 (c)(1),
(2), (4) Date: Jul. 19, 2000

(87) PCT Pub. No.: WO99/35991

PCT Pub. Date: Jul. 22, 1999

(30) Foreign Application Priority Data

Jan. 20, 1998 (NO) .......................................... 19980267

(51) Int. Cl.[7] .............................................. A61B 17/00
(52) U.S. Cl. ..................................... 606/1; 604/93.01
(58) Field of Search ........................... 606/1, 129, 172, 606/32, 108, 130, 167; 604/93.01, 174

(56) References Cited

U.S. PATENT DOCUMENTS

D292,021 S  * 9/1987 Stoll ............................ D24/16
5,006,122 A  * 4/1991 Wyatt et al. ......... 128/DIG. 26
5,056,523 A    10/1991 Hotchkiss, Jr. et al.
5,643,286 A    7/1997 Warner et al.

FOREIGN PATENT DOCUMENTS

NO            974274          9/1997
WO       WO 99/16374          4/1999

* cited by examiner

Primary Examiner—Teresa Walberg
Assistant Examiner—Thor Campbell
(74) Attorney, Agent, or Firm—Finnegan, Henderson, Farabow, Garrett & Dunner, L.L.P.

(57) ABSTRACT

The invention concerns a lock device for use in connection with elongated surgical instruments such as surgical needles, electrodes, etc., wherein the lock device consists of at least a first and a second distance member which surround the surgical instrument and a third stop member. All the parts are movable in the longitudinal direction relative to the instrument and thereby relative to one another, they are individually lockable in the depth position relative to the instrument and are equipped with indication devices for indication of position relative to one another, with the result that the instrument's movement in the longitudinal direction (depth) is controlled by controlling the distance for the relative movement between the distance members.

7 Claims, 5 Drawing Sheets

LOCK DEVICE FOR SURGICAL INSTRUMENTS

BACKGROUND OF THE INVENTION

The present invention concerns a lock device for use in connection with elongated surgical instruments such as surgical needles, electrodes, catheters, endoscopic equipment, etc.

In neurosurgical operations, for example, instruments are commonly inserted into the brain. These instruments must be positioned in a highly controlled manner with regard to adjustment of both angle and depth.

On the subject of angular orientation of surgical instruments we refer to the applicant's U.S. Pat. No. 6,328,748 which is hereby included as a reference in its entirety. This patent describes a holder for stereotactic equipment. The said holder is based on the use of a ball joint which permits angular adjustment of equipment. The ball has a channel through which the equipment is passed.

Several known locks are based on securing the instruments at a specific depth by placing a screw in between the instrument and a collar around it. Screw locks of this kind lead to great pressure over a small area on the instrument. If the instrument is a surgical needle, this can cause damage to the needle, which is hollow and therefore not particularly resistant to local pressure on the wall.

The lock which is employed here is a collar lock consisting of a round plate with two halves connected together in a joint and a screw which permit the parts to be separated from each other or to be joined together. When the parts are joined together, they are pressed together uniformly round the entire periphery of the instrument which is thereby locked to the collar in a particular position.

When the instrument is positioned in the operative field in, e.g., the brain, it may be desirable to move it in the longitudinal direction. This movement must be controlled and as precise as possible.

U.S. Pat. No. 5,056,523 describes a stereotactic frame system for positioning a probe tip relative to a target area in the body. The frame's co-ordinates for biopsy taking are set directly by looking at the area on an X-ray. A biopsy needle is attached to the frame by means of a screw lock. The needle is supported by an adaptor which passes down into an adaptor holder. The needle is further supported and passed through a plate with several holes. The single lock which is employed is not sufficient to provide accurate positioning and movement of the needle in the depth direction relative to the frame.

U.S. Pat. No. 5,643,286 discloses a microdrive for use in stereotactic surgery. This device comprises an external guiding frame, a stop element equipped with a ruler for measurement of distance, and an instrument holding element. When in use, the instrument will be guided by means of the frame, and the distance between the stop element and the instrument holding element will be read on the ruler. The device according to U.S. Pat. No. 5,643,286 comprises an external frame, which requires a lot of space, projects from the operative field, and includes several small parts.

There are many situations where it is desirable to enter the brain from below. In this case the ends of the various surgical instruments will be facing shoulders and neck. The instrument described in U.S. Pat. No. 5,643,286 will then come into conflict with these anatomical structures. For this reason it is important that the guiding arrangement for the instrument should not occupy more space than is absolutely necessary. The frame in U.S. Pat. No. 5,643,286 projects a long way out from the operative field, and this is disadvantageous since there is a greater possibility of brushing against the equipment by mistake. Such accidents can also cause significant damage. Moreover, the length of the frame is fixed, independent of the distance one wishes to measure. When small movements are carried out within the brain, the frame is unnecessarily large, which may lead to the above-mentioned disadvantages. In addition to this the frame restricts movement of the instrument in the longitudinal direction. The device cannot be used in connection with short needles, which are used for procedures in the shoulder and neck area. It is intended for use together with a stereotactic frame. When it is used in biopsy taking the above-mentioned device will be attached to a biopsy needle, where the needle's two upper parts must be capable of rotating freely and independently of each other for sampling. This is not possible when using this device. The device according to U.S. Pat. No. 5,643,286 also includes several parts which have to co-operate with a high degree of precision, and which have to be disinfected after use. This entails high production costs and considerable time consumption. The equipment cannot be used in several locations during the same operation without re-sterilisation.

SUMMARY OF THE INVENTION

The above-mentioned problems in the known devices have been solved by means of the lock device according to the present invention. This consists of at least a first and a second distance member and a stop member, where all parts are movable in the longitudinal direction relative to the instrument and thereby relative to one another, and are individually lockable in the depth position relative to the instrument. The lock device is characterized in that the distance members and the stop member surround the surgical instrument, which thereby forms a guiding frame for the said parts, and that integrated in the distance members there are indication devices for indicating the position of the members relative to each other.

BRIEF DESCRIPTION OF THE DRAWINGS

Embodiments of the invention are illustrated in the accompanying drawings, in which.

DETAILED DESCRIPTION OF THE INVENTION

Figure 1:
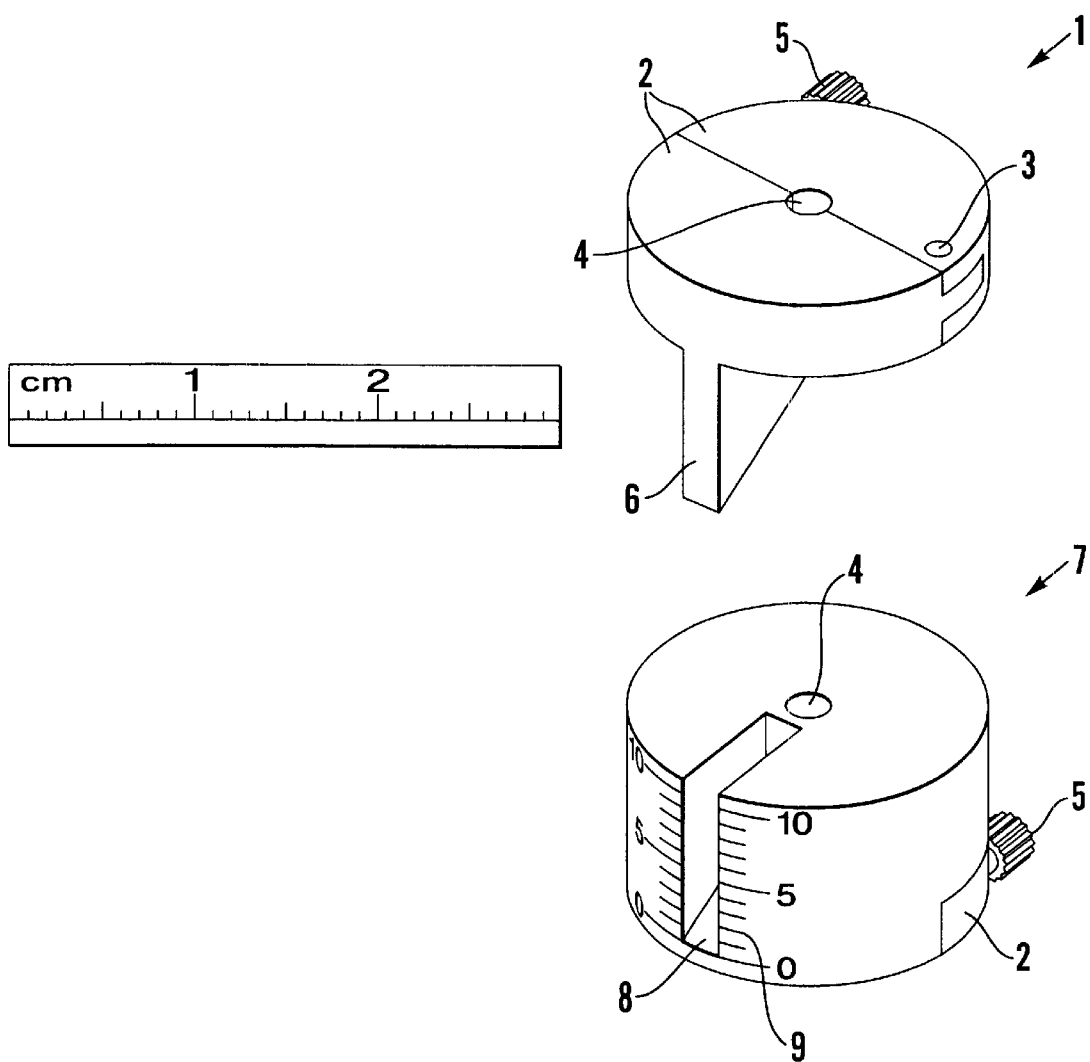
FIG. 1 is a view of a first embodiment of the invention, with the two distance members in a position apart from each other.

The lock device according to the invention permits implementation of a completely controlled movement.

During use the distance members, which in a preferred embodiment each comprise an integrated collar lock, and the stop member on the instrument will be arranged in such a manner that, for example, the distance members are located on top and the stop member is located at the bottom. The distance members abut against each other. In order to push the instrument downwards, the upper distance member is released and pulled upwards along the instrument for a specific distance (which is read off by means of the indication devices). The upper distance member is then attached to the instrument and the lower distance member released and attached to abut against the first distance member. Finally the stop member is released and the instrument is pushed downwards until the lower distance member comes into abutment against the stop member. When the instrument is lifted the stop member and second distance member are opened. The upper distance member which is locked is retracted together with the instrument. When the correct new setting has been achieved, the stop member and lower distance member are locked before the upper distance member is opened and lowered on to the lower distance member and relocked.

The terms "first and second distance member" are employed in the present description for the sake of clarity, and not in order to restrict the positioning of the distance members relative to the instrument's tip to a particular order.

The lock device according to the invention employs the elongated surgical instrument as a frame. The consequence of this is that the length of the combined equipment is determined by the length of the instrument, and this can be adapted to suit the application. Thus the device can be employed together with short needles, e.g. for procedures in the shoulder and neck area.

The device comprises distance indication devices integrated with the distance members, and is not dependent on external devices.

In a preferred embodiment the lock device occupies only 2 cm of the instrument's length, thus permitting movement of the instrument in its entire length.

By means of the lock device according to the invention a neurosurgical instrument, e.g., can be locked at a level which is as close as possible to the insertion point in the brain, thereby ensuring the best possible precision and most stable securing of the device.

The invention has a minimum of parts, and is therefore simple to manufacture and to disinfect.

The lock device according to the invention permits easy reading and setting of the distance, and can be used both ways (i.e. the distance members can change places relative to the instrument's tip). Simplicity of use and least possible chances of error are important since the measurement has to be performed in a stress situation, and it must be accurate.

The instrument can be rotated freely while the lock device keeps the distance to the operative field unaltered. This also applies for biopsy needles, where both parts of the needle can be rotated without interference from the lock device.

The invention also provides a triple locking of the instrument, resulting in increased safety during use.

There are several possible embodiments of the invention.

In a first preferred embodiment of the invention the first distance member comprises a collar and the second distance member a cylinder member and a similar collar. The collars in the first and second distance members are of the known type where two halves are hinged together by means of a pin and clamp around the instrument. The movement of the halves relative to each other is controlled by means of a screw. As mentioned before, the cylinder comprises such a collar and is attached in this manner to the instrument or may be released therefrom.

The indication devices in this preferred embodiment of the invention comprise a wedge-shaped protrusion on the first distance member and a recess equipped with a scale on the second distance member, so that the protrusion fits into the recess. By this means the distance between the distance members can be read off on the tip of the wedge-shaped protrusion in relation to the scale on the recess. In addition this embodiment controls the members' rotational position relative to each other.

In a second preferred embodiment of the invention the first distance member comprises an indication device in the form of a sheath. The second distance member comprises an indication device in the form of a cylinder with a scale. The sheath in the first distance member surrounds the cylinder in the second distance member, and the position indication is performed by viewing the position of the edge of the sheath relative to the cylinder's scale.

In a further preferred embodiment of the invention the first distance member comprises an indication device in the form of a pointer. The second distance member further comprises an indication device in the form of a cylinder equipped with a scale. The indication of position is performed by reading the pointer's position on the scale.

All the said embodiments of the invention permit rotary motion of the distance members relative to the stop member, and the two latter embodiments also permit rotary motion between the distance members. The distance members in the embodiments are preferably provided with collar members, but these can be replaced by other parts with the same function.

With regard to attachment of the distance members to the instrument, this may be performed, e.g., by means of a screw rod provided with a soft piston which is moved against the instrument and securely locked thereto.

The invention will now be described by means of embodiments. These embodiments are described in order to illustrate the invention and are by no means intended to limit the implementation of the invention.

FIG. 1 illustrates a first distance member 1 comprising a collar with two halves 2, which are hinged together round a pin 3. The collar is provided with a hole 4 for insertion of a surgical instrument and a screw 5 for securing the collar to the instrument, or releasing the collar from the instrument. The indication devices in this first distance member 1 comprise a wedge-shaped protrusion 6 for control of movement and indication of position.

The second distance member 7 comprises a cylinder which is provided with a corresponding collar at one of the cylinder's ends. The indication devices in the second distance member 7 comprise a recess 8 which will receive the protrusion 6 in the distance member 1. Round the recess 8 there is placed a scale 9 which indicates the relative distance between the parts.

Figure 2:
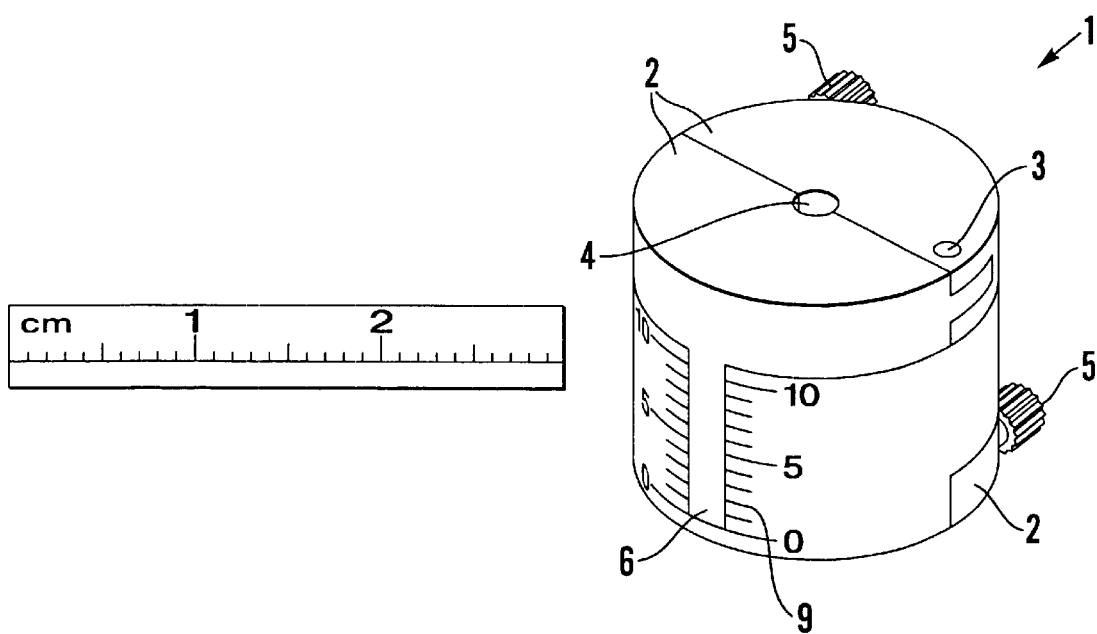
FIG. 2 is a view of the same embodiment, with the two distance members put together.

FIG. 2 illustrates the distance members in a combined state. It can be seen that since the distance between the distance members is zero, the tip of the wedge-shaped protrusion 6 will be located on the zero mark on the scale 9.

As mentioned before, by this means a highly controlled movement of the instrument is obtained in a simple manner. The adjustment is easy, with only two screws having to be handled.

Figure 3:
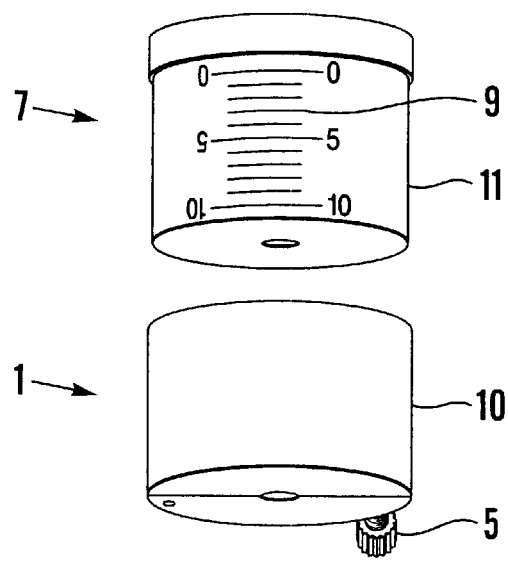
FIG. 3 is a view of a second embodiment of the invention, with the two distance members apart from each other.

FIG. 3 illustrates a second embodiment of the invention, where the first distance member 1 comprises an indication device with a sheath 10. The second distance member 7 comprises an indication device in the form of a cylinder 11, with the sheath 10 surrounding the cylinder 11. The cylinder 11 is equipped with a scale 9.

Figure 4:
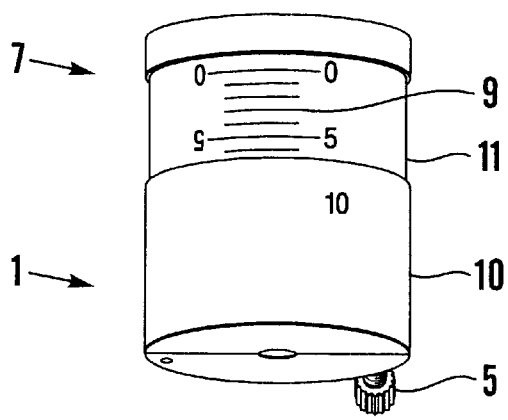
FIG. 4 is a view of the embodiment illustrated in FIG. 3, with the distance members "connected" to each other.

FIG. 4 illustrates how the parts 1 and 7, and thereby the devices 10 and 11 cooperate with each other. The distance between the parts can be read by means of the scale 9 and the edge of the sheath 10.

Figure 5:
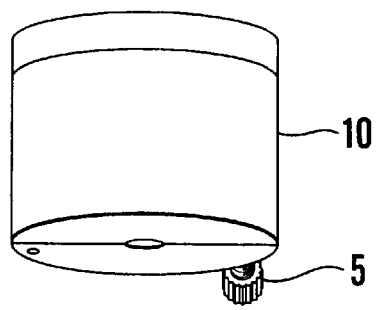
FIG. 5 is a view of the embodiment illustrated in FIGS. 3 and 4, with the two distance members put together.

FIG. 5 illustrates the parts 1 and 7 put together. This embodiment of the invention permits the parts to rotate relative to each other.

Figure 6:
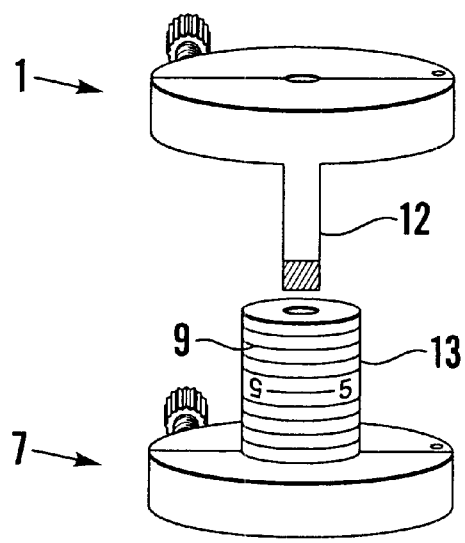
FIG. 6 is a view of a third embodiment of the invention, with the two distance members apart from each other.

FIG. 6 illustrates a third embodiment of the invention. In this embodiment the first distance member 1 comprises an indication device in the form of a pointer 12. The second distance member 7 comprises an indication device in the form of a cylinder 13 equipped with a scale 9.

Figure 7:
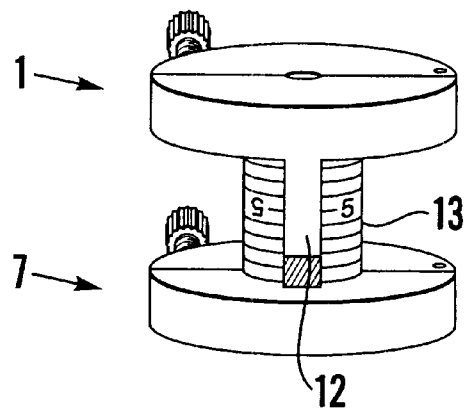
FIG. 7 is a view of the embodiment illustrated in FIG. 6, with the distance members "connected" to each other.

FIG. 7 illustrates the parts put together.

Figure 8:
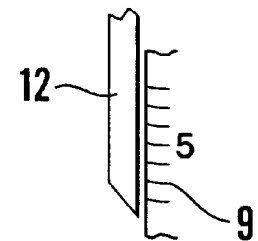
FIG. 8 illustrates the pointer in the third embodiment of the invention viewed from the side.

FIG. 8 illustrates the pointer 12 in detail. As shown in the figure, in a preferred embodiment the pointer's tip has an angled surface which permits easier visualisation of the position of the pointer's tip on the scale 9.

This third embodiment of the invention may be implemented with very low weight, which is a considerable advantage. The design permits rotation of the distance members relative to each other.

Figure 9:
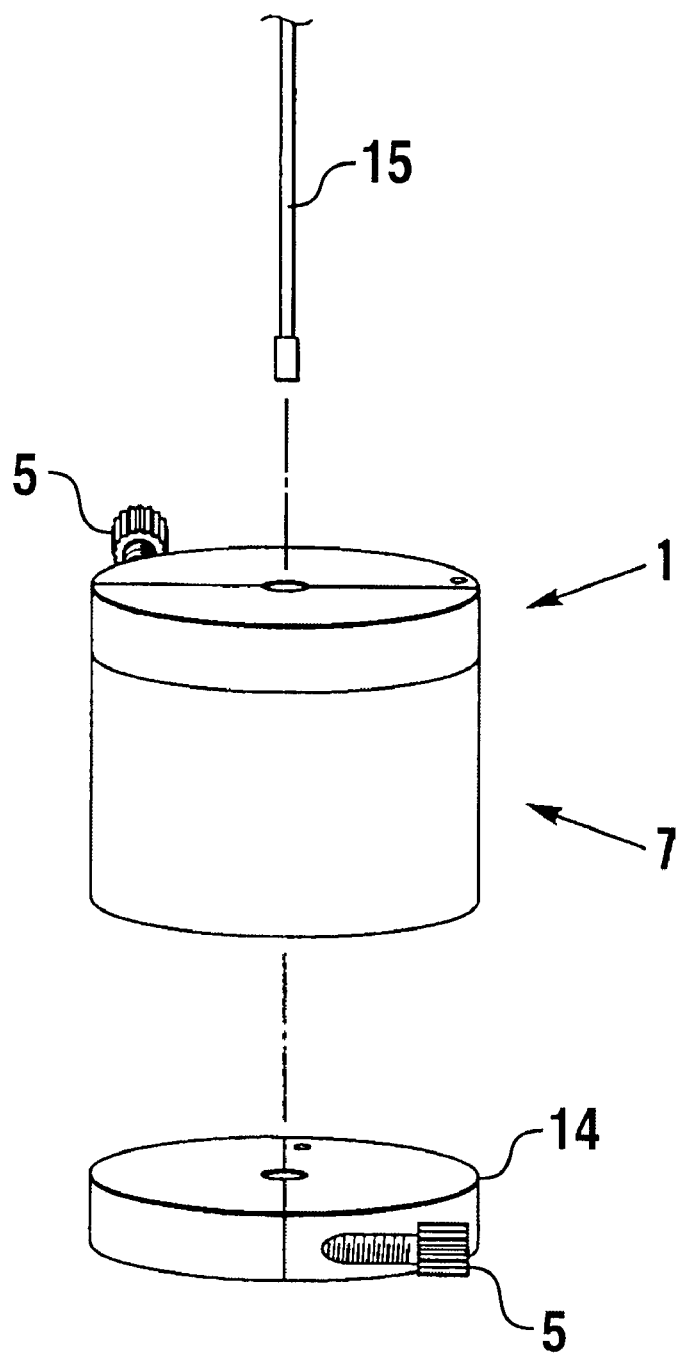
FIG. 9 shows the relationship between the distance members, the stop member, and an elongated surgical instrument.

FIG. 9 illustrates the relationship between first distance member 1, second distance member 7, stop member 14, and an elongated surgical instrument 15.

As illustrated by the description above, the invention represents an excellent lock device for precise, safe and simple depth positioning of surgical instruments.

What is claimed is:

1. A lock device for use in connection with elongated surgical instruments, said lock device comprising at least a first and a second distance member and a stop member, all members being movable in a longitudinal direction relative to the instrument and thereby relative to one another, means for individually locking each member in a position relative to the instrument, wherein the distance members and the stop member surround the surgical instrument, the instrument thereby forming a guiding frame for said members, and indication means on said distance members for indicating the position of the distance members relative to one another.

2. The lock device according to claim 1, wherein the distance members comprise collar locks comprising two halves hinged together by means of a pin and which are locked against the instrument by means of a screw.

3. The lock device according to claim 1, wherein the stop member is a collar lock.

4. The lock device according to claim 1, wherein the indication means comprise a wedge-shaped protrusion on the first distance member and a recess on the second distance member, the recess being able to receive the protrusion and having a scale that cooperates with the protrusion to indicate the position of the distance members relative to each other.

5. The lock device according to claim 1, wherein the indication means comprise a sheath in the first distance member for surrounding the second distance member, and a cylinder having a scale on the second distance member, the cylinder cooperating with the sheath for indicating the position of the distance members relative to each other.

6. The lock device according to claim 1, wherein the indication means comprise a pointer on the first distance member and a cylinder having a scale on the second distance member, the pointer cooperating with the cylinder for indication of the position of the distance-members relative to each other.

7. The lock device according to claim 1, wherein said device is made of surgical steel.

* * * * *